(12) United States Patent
Lin et al.

(10) Patent No.: US 7,435,543 B2
(45) Date of Patent: Oct. 14, 2008

(54) GENETIC MARKERS FOR PIG BACKFAT THICKNESS

(75) Inventors: En-Chung Lin, Miaoli Hsien (TW); Ming-Yu Chen, Miaoli Hsien (TW); San-Yuan Huang, Miaoli Hsien (TW); Hui-Liang Tsou, Miaoli Hsien (TW); Wen-Chuan Lee, Miaoli Hsien (TW)

(73) Assignee: Animal Technology Institute of Taiwan, Miaoli Hsien (TW)

( * ) Notice: Subject to any disclaimer, the term of this patent is extended or adjusted under 35 U.S.C. 154(b) by 313 days.

(21) Appl. No.: 10/958,837

(22) Filed: Oct. 5, 2004

(65) Prior Publication Data

US 2005/0112648 A1    May 26, 2005

Related U.S. Application Data

(63) Continuation-in-part of application No. 09/995,026, filed on Nov. 27, 2001, now abandoned.

(51) Int. Cl.
C12Q 1/68 (2006.01)
C07H 21/04 (2006.01)
C12P 19/34 (2006.01)

(52) U.S. Cl. .......................... 435/6; 536/24.3; 435/91.2
(58) Field of Classification Search .................. 435/6; 536/24.3
See application file for complete search history.

(56) References Cited

OTHER PUBLICATIONS

Maak et al. 1998. Animal Genetics 29 (Suppl. 1) 60-74.*
Maak et al. 1999. Arch. Tierz., Dummerstorf 42(1999) Special Issue, 141-143.*
Roan, et al., "A Survey on the Antibiotic Residues in Pork in the Middle Part of Taiwan," Journal of Chin. Soc. Anim. Sci. (1980), pp. 55-69 (1-2).
Lindquist, et al., "The Heat-Shock Proteins," Annu. Rev. Genet. (1988), pp. 632-677, vol. 22.
Welch, William J., "Mammalian Stress Response: Cell Physiology, Structure/Function of Stress Proteins, and Implications for Medicine and Disease," Physiological Review (1992), pp. 1063-1081, vol. 72, No. 4.
Schwerin, et al., "The Inducible Stress Protein 70.2 Gene—A Candidate Gene for Stress Susceptibility in Swine," Arch. Animal Breed. (1999), pp. 61-66, vol. 42.
Huang, et al., "Association of Heat Shock Protein 70 with Semen Quality in Boars," Animal Reproduction Science (2000), pp. 231-240, vol. 63.
Peelman, Luc J., et al., "Complete nucleotide sequence of a porcine HSP70 gene," Immunogenetics, (1992) pp. 286-289, vol. 35, No. 4.
Maak, et al., Animal Genetics (1998) 29 (Suppl. 1) 60-74.
Maak, et al., Arch. Tierz., Dummerstorf 42 (1999) Special Issue, pp. 141-143.
Chen M.Y., et al., "Polymorphism in the 5'-flanking region of porcine heat shock protein 70.2 gene," Animal Genetics (2000) pp. 404-419, vol. 31.
Ulbrecht et al., Asociation of B2-Adrenoreceptor Variants with Bronchial Hyperresponsiveness, American Journal of Respiratory and Critical Care Medicine, vol. 161, pp. 469-474 (2000).
GenBank Accession AF139178, GI: 5031272, Sus scrofa heat shock protein 70.2 gene, promoter and partial cds. Jul. 3, 2001.

* cited by examiner

Primary Examiner—Sarae Bausch
Assistant Examiner—Steven C Pohnert
(74) Attorney, Agent, or Firm—Cook Alex Ltd.

(57) ABSTRACT

The present invention provides a method of screening pigs to identify those which have a genetic predisposition to have a thinner or thicker backfat thickness by assaying the pattern of the five single nucleotide polymorphisms in the HSP70.2 gene that is associated with backfat thickness.

1 Claim, 1 Drawing Sheet

| | | |
|---|---|---|
| Schwerin AJ309021 | -acaggtgccgtgcaaac-gcgaaacctccacagcatctcttccccctcccttgaggaa | 58 |
| Chen AF139178 | aacaggtgccgtgcaaacagcgaa-cctccacagcatctcttccccctcccttgagga- | 58 |
| SEQ ID No: 1 | aacaggtgccgtgcaaacagcgaa-cctccacagcatctcttccccctcccttgagga- | 58 |
| | 44 | |
| Schwerin AJ309021 | ctccggtttcctcccgcgaatcccagaagagtctggagagttctgggaggggcggcagcc | 118 |
| Chen AF139178 | ctccggtttcctcccgcgaatcccagaagagtctggagagttctgggaggggcggcagcc | 118 |
| SEQ ID No: 1 | ctccggtttcctcccgcgaatcccagaagagtctggagagttctgggaggggcggcagcc | 118 |
| Schwerin AJ309021 | agggcgctgattggccccagaaagccagggggcaggacgcgaggcgaaacctctggaata | 178 |
| Chen AF139178 | agggcgctgattggccccagaaagccagggggcaggacgcgaggcgaaacctctggaata | 178 |
| SEQ ID No: 1 | agggcgctgattggccccagaaagccagggggcaggacgcgaggcgaaacctctggaata | 178 |
| Schwerin AJ309021 | ttcccgacctggcagccccgccgagctcggggattggctgaggagggaaaaggcggggct | 238 |
| Chen AF139178 | ttcccgacctggcagccccgccgagctcggggattggctgaggagggaaaaggaggggct | 238 |
| SEQ ID No: 1 | ttcccgacctggcagccccgccgagctcggggattggctgaggagggaaaaggaggggct | 238 |
| | 232 | |
| Schwerin AJ309021 | tgaggaaaaaaatataaacacagagccgcccccagggaaacagcgagcccgggaagagct | 298 |
| Chen AF139178 | tgaggaaaaaaatataaacacagagccgcccccagggaaacagcgagcccgggaagagct | 298 |
| SEQ ID No: 1 | tgaggaaaaaaatataaacacagagccgcccccagggaaacagcgagcccgggaagagct | 298 |
| | 250 | |
| Schwerin AJ309021 | gctaagacttcctctgcggtctgtgagcgcagccttggcagatccgttgcctccgaggac | 358 |
| Chen AF139178 | gctaagacttcctctgcggtctgtgagcgcagccttggcagatccgctgcctccgaggac | 358 |
| SEQ ID No: 1 | gctaagacttcctctgcggtctgtgagcgcagccttggcagatccgctgcctccgaggac | 358 |
| | 345 | |
| Schwerin AJ309021 | caccgcgggcagaagcggcgcgttcggtttccggcttcagagctctcgtctgggatcccg | 418 |
| Chen AF139178 | caccgcgggcagaagcggcgcgttcggtttccggcttcagagctctcgtctgggatcccg | 418 |
| SEQ ID No: 1 | caccgcgggcagaagcggcgcgttcggtttccggcttcagagctctcgtctgggatcccg | 418 |
| | 393 | |
| Schwerin AJ309021 | gtttcgagtctagaggctgtttgcggagagagcaggccagcgac | 462 |
| Chen AF139178 | gtttcgagtctagaggctgtttgcggagagagcaggccagcgac | 462 |
| SEQ ID No: 1 | gtttcgagtctagaggctgtttgcggagagagcaggccagcgac | 462 |

Figure 1

GENETIC MARKERS FOR PIG BACKFAT THICKNESS

CROSS-REFERENCE TO RELATED APPLICATIONS

This is a continuation-in part of U.S. patent application Ser. No. 09/995,026, filed Nov. 27, 2001 now abandoned.

FIELD OF THE INVENTION

This invention relates generally to genetic markers for pig backfat thickness. In particular, the invention relates to a method of screening pigs to identify those which have a genetic predisposition to have a thinner or thicker backfat thickness.

DESCRIPTION OF THE PRIOR ART

The heat shock protein 70 (HSP70) is the most abundant and highly conserved HSP in all organisms studied so far. The expression of HSP70 in eukaryotic cells is encoded by a multigene family and can be divided into constitutively expressed and stress-inducible forms (Lindquist and Craig, Annu. Rev. Genet. 22: 63-77, 1988); (Welch, Physiol. Rev. 72: 1063-1081, 1992). HSP70 has been proved to be important in thermotolerance. HSP70 level has also been found to be possibly associated with semen quality in boars (Huang et al., Anim. Reprod. Sci. 63: 231-240, 2000).

Peelman et al. (Immunogenetics 35: 286-9, 1992) first reported the complete nucleotide sequence of porcine HSP70.2 gene. Two polymorphic sites in the 5'flanking region of porcine HSP70.2 have been found by Schwerin et al. (Arch. Anim. Breed. 42: 61-66, 1999), and five single nucleotide polymorphisms (SNPs) at sites 44, 232, 250, 345 and 393 in the 5'-flanking region of porcine HSP70.2 gene have also been identified (Chen et al., Anim. Genet. 31: 410-411, 2000). However, none of the prior art references disclosed that the polymorphic sites were associated with backfat thickness.

SUMMARY OF THE INVENTION

It is an object of the invention to provide a method of screening pigs to identify those which have a genetic predisposition to have a thinner or thicker backfat thickness. In particular, the method of the present invention comprises the steps of obtaining a sample of genomic DNA from a pig, and assaying for the presence of polymorphisms in porcine HSP70.2 gene in said sample, said polymorphisms being associated with pig backfat thickness, wherein the polymorphic sites are the sites corresponding to sites 44, 232, 250, 345 and 393 in the 5'-flanking region of porcine HSP70.2 gene of SEQ ID NO.: 1, and the polymorphic sites being CCATT or CC-TC indicates a genetic predisposition to have a thinner backfat thickness; while the polymorphic sites being CCATC or AAACC indicates a genetic predisposition to have a thicker backfat thickness.

Another object of the invention is to provide a method of screening pigs to identify those which have a genetic predisposition to have a thin backfat thickness by assaying for the presence of a specific genotype being CCATT/CCATT, CCATT/CC-TC, CCATT/CCATC, CCATT/AAACC or CC-TC/CC-TC at the sites corresponding to sites 44, 232, 250, 345 and 393 in the 5'-flanking region of porcine HSP70.2 gene of SEQ ID NO.: 1.

The invention also provides a method of screening pigs to identify those which have a genetic predisposition to have a thick backfat thickness by assaying for the presence of a genotype being CC-TC/AAACC, CCATC/CCATC, or CCATC/AAACC at the sites corresponding to sites 44, 232, 250, 345 and 393 in the 5'-flanking region of porcine HSP70.2 gene of SEQ ID NO.: 1.

The details of the invention are set forth in the description below. Other features, objects, and advantages of the invention will be apparent from the description and the claims.

BRIEF DESCRIPTION OF THE DRAWING

FIG. 1 shows the multiple sequence alignment for three sequences of the 5'-flanking region of procine HSP70.2 gene, wherein SEQ ID NO.: 1 is the sequence referred to in the present invention, AJ309021 was identified by Schwerin et al. (1995) (SEQ ID NO.: 2 in the attached Sequence Listing) and AF139178 was identified by Chen et al. (2000) (SEQ ID NO.: 3 in the attached Sequence Listing).

DETAILED DESCRIPTION OF THE INVENTION

The term "polymorphism," as used herein, refers to a variation in nucleotide sequence (and encoded polypeptide sequence, if relevant) at a given position in the genome within a population.

The term "single nucleotide polymorphism (SNP)," as used herein, refers to the occurrence of nucleotide variability at a single nucleotide position in the genome, within a population. A SNP occurs within a gene or within intergenic regions of the genome.

The term "5'-flanking region of porcine HSP70.2 gene," as used herein, refers to the upstream sequence of porcine HSP70.2 gene, which contains two consensus sequences of heat shock element along with two regions with homology to the CCAAT box, two binding sites for transcription factor SP1, and a TATA box. The 5'-untranslated leader sequence of the porcine HSP70.2 gene has a GC content of 64% and is 91% homogenous with the sequence reported by Peelman et al (Immunogenetics 35, 286-9, 1992). In a preferred embodiment of the invention, the "5'-flanking region of porcine HSP70.2 gene" is of the nucleotide sequence denoted by SEQ ID NO.: 1. FIG. 1 provides the multiple sequence alignment for three sequences of the 5'-flanking region of porcine HSP70.2 gene. Persons skilled in the art can readily obtain the nucleotide sequences of the 5'-flanking region of porcine HSP70.2 gene through any standard methods or technologies well known to those skilled in the art.

The term "polymorphic sites" as used herein, refers to the sites corresponding to sites 44, 232, 250, 345 and 393 in the 5'-flanking region of porcine HSP70.2 gene of SEQ ID NO.:1. The polymorphic sites may also refer to the corresponding sites of any native occurring 5'-flanking region of porcine HSP70.2 gene.

The term "backfat thickness (BF)," as used herein, refers to a value measured on both sides of the following positions: behind the scapula, last rib and lumbar vertebra. BF is corrected for weight as follows (Chyr, S. C., 1980, J. Chin. Soc. Anim. Sci., 9:55-69):

$$BF = \text{average backfat thickness (mm)} \times [1 + 0.0088184 \times (110 - \text{end-test body weight(kg)})]$$

The term "thinner or thicker backfat thickness," as used herein, means a biologically, significantly thinner or thicker backfat thickness than the mean of a given population. For instance, the mean backfat thickness of male pigs is around 1.41±0.12 cm. The means of backfat thickness of the groups with the genotypes being CCATT/CCATT, CCATT/CC-TC, CCATT/CCATC, CCATT/AAACC and CC-TC/CC-TC (ranging from 1.31 cm to 1.39 cm), are thinner than the mean of the all animals (1.41 cm). To the contrary, the means of backfat thickness of the groups with the genotypes being CC-TC/AAACC, CCATC/CCATC and CCATC/AAACC (ranging from 1.48 cm to 1.53 cm), are thicker than the mean of the all animals (1.41 cm).

The term "cool weather" as used herein, refers to the weather in the period between November and April with a low temperature range of 12-19° C. and a high temperature of 19-25° C.

This invention is based on the discovery of genetic markers associated with pig backfat thickness, which markers are the combinations of five single nucleotide polymorphisms at the sites corresponding to the nucleotide sites 44, 232, 250, 345 and 395 in the 5'-flanking region of porcine HSP70.2 gene of SEQ ID NO.: 1. As demonstrated in the results given in Table 1 (discussed below), if the five single nucleotide polymorphisms at the sites corresponding to the nucleotide sites 44, 232, 250, 345 and 395 in the 5'-flanking region of porcine HSP70.2 gene of SEQ ID NO.: 1, are CCATT or CC-TC (wherein "-" denotes deletion), respectively, the pig would more likely have a significantly thin backfat thickness; while the polymorphisms are CCATC or AAACC, respectively, the pig would more likely have a significantly thick backfat thickness.

The present invention features the use of the combinations of the five single nucleotide polymorphisms in the 5'-flanking region of porcine HSP70.2 gene as genetic markers for pig backfat thickness. According to the invention, the presence of the five single nucleotide polymorphisms at the sites corresponding to the nucleotide sites 44, 232, 250, 345 and 395 in the 5'-flanking region of porcine HSP70.2 gene of SEQ ID NO.: 1 being CCATT or CC-TC indicates a genetic predisposition to have a thin backfat thickness, while the five single nucleotide polymorphisms being CCATC or AAACC indicates a genetic predisposition to have a thick backfat thickness. According to Table 1, the effect of the polymorphisms on backfat thickness is more significant in cool weather.

The invention provides a method of screening pigs to identify those which have a genetic predisposition to have a thinner, or thicker backfat thickness, comprising the steps of (a) obtaining a sample of genomic DNA from a pig; and (b) assaying for the presence of polymorphisms in porcine HSP70.2 gene in said sample, said polymorphisms being associated with pig backfat thickness;

wherein the polymorphic sites are the sites corresponding to sites 44, 232, 250, 345 and 393 in the 5'-flanking region of porcine HSP70.2 gene of SEQ ID NO.: 1, and the polymorphic sites being CCATT or CC-TC indicates a genetic predisposition to have a thinner backfat thickness; while the polymorphic sites being CCATC or AAACC indicates a genetic predisposition to have a thicker backfat thickness.

The present invention also provides a method of screening pigs to identify those which have a genetic predisposition to have a thin backfat thickness, comprising the steps of (a) obtaining a sample of genomic DNA from a pig; and (b) assaying for the presence of a genotype being CCATT/CCATT, CCATT/CC-TC, CCATT/CCATC, CCATT/AAACC or CC-TC/CC-TC at the sites corresponding to sites 44, 232, 250, 345 and 393 in the 5'-flanking region of porcine HSP70.2 gene of SEQ ID NO.: 1, in said sample.

The present invention also provides a method of screening pigs to identify those which have a genetic predisposition to have a thick backfat thickness, comprising the steps of (a) obtaining a sample of genomic DNA from a pig; and (b) assaying for the presence of a genotype being CC-TC/AAACC, CCATC/CCATC, or CCATC/AAACC at the sites corresponding to sites 44, 232, 250, 345 and 393 in the 5'-flanking region of porcine HSP70.2 gene of SEQ ID NO.: 1, in said sample.

Any method of assaying for the presence of polymorphisms may be used in the present invention. Such methods include one that analyzes the polymorphic gene product and detects polymorphisms by determining the resulting differences in the gene product.

According to the present invention, a sample of genomic DNA is obtained from a pig for assaying polymorphisms. Generally, blood cells are used as the source of the DNA. A sufficient amount of DNA for analysis can be determined by persons skilled in the art and the techniques for DNA isolation are also known to persons skilled in the art. In certain instances, it may be desirable to amplify the amount of DNA through the use of standard techniques, such as the polymerase chain reaction (PCR).

In one preferred embodiment, the purified PCR products are sequenced in both directions, and the nucleotide sequences are recorded with an automated DNA sequencer.

The invention will be described in detail by reference to the following non-limiting examples.

EXAMPLE

Animals

The 205 purebred Duroc pigs used in this study were obtained from 11 purebred farms in Taiwan. Genetic relationships between the pigs were avoided as much as possible. The pigs were sent to the Northern Central Testing Station at the Pig Research Institute Taiwan in 5 batches using the segregated early weaning (SEW) entrance method (July, September, November, December 1999 and March 2000). The weight and entry age were limited to 4-9 kg (5.94±1.35kg in average) and 14-20 days (17.2±2.1 days in average), respectively. The tested piglets were raised in the modular SEW nursery (Double L Group Inc.) for about 42 days and then moved to the testing house.

The tested pigs started the performance tests at a body weight of 30.0±2.0 kg. The tests were ended when the pigs reached a body weight of 110.0±2.0 kg. Each tested pig was kept in a pen of 4 m² in size. Altogether, there are 6 testing houses at the central testing station. Each house has 66 pens, allowing the animals from the same batch to be kept in the same house. All the tested pigs were fed ad libitum with the same diet of crude protein 18.5%, metabolizable energy 3,140 kcal/kg, calcium 1.20%, phosphorus 0.80%, lysine 1.06%, methionine 0.41%, cystine 0.30% and tryptophan 0.20%. The temperature at the testing house and the daily feed intake were recorded daily.

Determination of Backfat Thickness

At the end of the performance test (when the pigs reached 110±2 kg of body weight), backfat thickness of the tested pigs was measured using A-mode ultrasonic machine on both sides of the following positions: behind the scapula, last rib and lumbar vertebra. BF is corrected for weight as follows (Chyr, S. C., 1980, J. Chin. Soc. Anim. Sci., 9:55-69):

$$BF = \text{average backfat thickness (mm)} \times [1+0.0088184 \times (110-\text{end-test body weight(kg)})]$$

DNA Isolation and Sequencing

Genomic DNA was isolated from blood of the tested pigs using a DNA isolation kit for mammalian blood (Boehringer Mannheim, Ind., USA). The primers used in this experiment were designed according to the HSP70 gene sequence reported by Peelman et al. (1992). The reaction conditions for PCR followed the procedure set up by Chen et al. (2000). The PCR products were purified from gels using a gel extraction miniprep kit (Viogene, Sunnyvale, Calif., USA), and used in the following sequencing. The purified PCR products were sequenced in both directions, and the nucleotide sequences were recorded with an automated DNA sequencer (ABI 377, Perkin-Elmer, Forster, Calif., USA).

Statistical Analysis

The statistical model includes a season effect in the performance test, namely: cool weather (the whole test period between November and April with a low temperature range of 12-19° C. and a high temperature of 19-25° C.). One hundred and eighty-three animals with the nine major genotypes were tested. Meanwhile, the performance traits of those 183 animals were compared in the statistical analysis.

The trait of backfat thickness was analyzed by using a linear model with SAGE (days of age at the test started) as a covariate along with the test season, the genotype of the 5'-flanking region of HSP70.2, and interaction between the genotype and test season. The statistical analysis was conducted by using SAS GLM procedure (SAS Institute, 1989). The effects of regional genotype and its interaction with season were also compared using the least-squares means method.

Results

The least squares means (LSMs) of backfat thickness (BF) in those Duroc pigs tested are shown in Table 1. Particularly, the means for BF of those pigs were significantly different ($p<0.01$) among those genotypes in cool weather.

TABLE 1

The least squares means and comparison of different genotypes for BF of all the animals in the analysis and those tested in cool weather.

| Genotype* | BF | |
|---|---|---|
|  | All animals[1] | Cool weather[2] |
| CCATT/CCATT (10, 5) | $1.35 \pm 0.04^{ab}$ | $1.30 \pm 0.05^{a}$ |
| CCATT/CC-TC (14, 8) | $1.35 \pm 0.03^{ab}$ | $1.40 \pm 0.04^{abc}$ |
| CCATT/CCATC (53, 22) | $1.39 \pm 0.02^{ab}$ | $1.44 \pm 0.02^{bc}$ |
| CCATT/AAACC (9, 3) | $1.37 \pm 0.04^{ab}$ | $1.39 \pm 0.07^{abc}$ |
| CC-TC/CC-TC (8, 4) | $1.31 \pm 0.04^{a}$ | $1.36 \pm 0.06^{ab}$ |
| CC-TC/CCATC (39, 14) | $1.41 \pm 0.02^{bc}$ | $1.49 \pm 0.03^{cd}$ |
| CC-TC/AAACC (6, 3) | $1.53 \pm 0.05^{d}$ | $1.63 \pm 0.07^{de}$ |
| CCATC/CCATC (28, 7) | $1.48 \pm 0.03^{d}$ | $1.58 \pm 0.04^{e}$ |
| CCATC/AAACC (16, 10) | $1.48 \pm 0.03^{cd}$ | $1.61 \pm 0.04^{e}$ |
| Total (183, 76) | $1.41 \pm 0.01$ | $1.47 \pm 0.01$ |

[1]Values across the cells in the column of "All animals" with different letters of a, b, c, d in superscription mean significant difference with $p<0.05$.
[2]Values across the cells in the column of "Cool weather" with different letters of a, b, c, d, e in superscription mean significant difference with $p<0.01$.
**Values in the parentheses are the numbers of observations for those genotypes in all the animals included in the analysis and in the cool weather, respectively.

The values of backfat thickness (BF) of 183 Duroc pigs with 9 genotypes tested were measured and collected, the LSMs of BF showed a more significant level ($p<0.01$) using genotypes including the combination of the five single nucleotide polymorphisms. It is indicated in Table 1 that the polymorphic sites being CCATT or CC-TC indicates a genetic predisposition to have a thinner backfat thickness; while the polymorphic sites being CCATC or AAACC indicates a genetic predisposition to have a thicker backfat thickness. It is also shown in Table 1 that the genotype being CCATT/CCATT, CCATT/CC-TC, CCATT/CCATC, CCATT/AAACC or CC-TC/CC-TC at the sites corresponding to sites 44, 232, 250, 345 and 393 in the 5'-flanking region of porcine HSP70.2 gene of SEQ ID NO.: 1 has a genetic predisposition to have a significantly thin backfat thickness, and the genotype being CC-TC/AAACC, CCATC/CCATC, or CCATC/AAACC has a genetic predisposition to have a significantly thick backfat thickness.

Table 2 provides the effect of only one single nucleotide polymorphism at each of the five polymorphic sites in the 5' flanking region of HSP70.2 gene on backfat thickness (BF).

TABLE 2

The effects of three genotypes of each of those five polymorphic sites in the 5' flanking region of HSP70.2 gene on backfat thickness (BF).

| Mutation site | | BF |
|---|---|---|
| P44 | A/A (4) | $1.40 \pm 0.06^{de}$ |
|  | A/C (32) | $1.46 \pm 0.03^{d}$ |
|  | C/C (169) | $1.39 \pm 0.02^{e}$ |

TABLE 2-continued

The effects of three genotypes of each of those five polymorphic sites in the 5' flanking region of HSP70.2 gene on backfat thickness (BF).

| Mutation site | | BF |
|---|---|---|
| P232 | A/A (4) | $1.40 \pm 0.06^{de}$ |
| | A/C (32) | $1.46 \pm 0.03^{d}$ |
| | C/C (169) | $1.39 \pm 0.02^{e}$ |
| P250 | A/A (123) | $1.41 \pm 0.02^{a}$ |
| | A/− (72) | $1.40 \pm 0.02^{a}$ |
| | −/− (10) | $1.31 \pm 0.04^{b}$ |
| P345 | C/C (7) | $1.43 \pm 0.05^{ab}$ |
| | T/C (33) | $1.45 \pm 0.03^{a}$ |
| | T/T (165) | $1.39 \pm 0.02^{b}$ |
| P393 | C/C (111) | $1.42 \pm 0.02^{a}$ |
| | T/C (81) | $1.37 \pm 0.02^{b}$ |
| | T/T (13) | $1.37 \pm 0.04^{ab}$ |

*Values across those genotypes within a mutation site with superscription of a/b or d/e mean significant difference with $p < 0.05$ or $p < 0.1$.

After a comparison between the results given in Table 1 and Table 2, it is concluded that only one single nucleotide polymorphism gave a less significant level ($p<0.1$ or $p<0.05$) than that of the combination of the five single nucleotide polymorphisms.

That which is claimed:

1. A method of screening a population of Duroc pigs for genetic predisposition of backfat thickness comprising:
   a) obtaining a sample of genomic DNA from the Duroc Pigs;
   b) detecting the presence of polymorphism in the porcine HSP70.2 5'-flanking region comprising SEQ ID NO 1 at nucleotides 44, 232, 250, 345 and 393;
   c) identifying the genotype of CCATT/CCATT, CCATT/CC-TC, CCATT/CCATC, CC-TC/CC-TC, or CCATT/AAACC whereby said genotypes indicates the Duroc pigs having a genetic predisposition to backfat thickness less than Duroc pigs with genotypes CC-TC/AAACC, CCATC/CCATC or CCATC/AAACC.

* * * * *

SEQUENCE LISTING

```
<160> NUMBER OF SEQ ID NOS: 3

<210> SEQ ID NO 1
<211> LENGTH: 462
<212> TYPE: DNA
<213> ORGANISM: Sus scrofa
<220> FEATURE:
<221> NAME/KEY:
<222> LOCATION:
<223> OTHER INFORMATION:

<400> SEQUENCE: 1
aacaggtgcc gtgcaaacag cgaacctcca cagcatctct tccccctcc cttgaggact      60 ccggtttcct cccgcgaatc ccagaagagt ctggagagtt ctgggagggg cggcagccag     120
ggcgctgatt ggccccagaa agccaggggg caggacgcga ggcgaaacct ctggaatatt     180
cccgacctgg cagccccgcc gagctcgggg attggctgag gagggaaaag gagggcttg     240 aggaaaaaaa tataaacaca gagccgcccc cagggaaaca gcgagcccgg gaagagctgc     300
taagacttcc tctgcggtct gtgagcgcag ccttggcaga tccgctgcct ccgaggacca     360
ccgcgggcag aagcggcgcg ttcggtttcc ggcttcagag ctctcgtctg ggatcccggt     420
ttcgagtcta gaggctgttt gcggagagag caggccagcg ac                       462

<210> SEQ ID NO 2
<211> LENGTH: 462
<212> TYPE: DNA
<213> ORGANISM: Sus scrofa
<220> FEATURE:
<221> NAME/KEY:
<222> LOCATION:
<223> OTHER INFORMATION:
<300> PUBLICATION INFORMATION:
<301> AUTHORS: Schwerin,M.,
      Lengerken,G.,
      Fredholm,M.,
      Christensen,K.
      Krause,S.
<302> TITLE: DNA polymorphisms in two transcription control elements
      (SP1- and TATA-box) of porcine HSP70.2 gene detected by allele-
      specific PCR
<303> JOURNAL: Animal genetics
<304> VOLUME: 26
<305> ISSUE: 3
<306> PAGES: 203-204
<307> DATE: 1995
<308> DATABASE ACCESSION NUMBER: AJ309021; GenBank
<309> DATABASE ENTRY DATE: 2001-03-29
```

-continued

```
<400> SEQUENCE: 2
acaggtgccg tgcaaacgcg aaacctccac agcatctctt ccccccctccc ttgaggaact    60 ccggtttcct cccgcgaatc ccagaagagt ctggagagtt ctgggagggg cggcagccag   120
ggcgctgatt ggccccagaa agccaggggg caggacgcga ggcgaaacct ctggaatatt   180
cccgacctgg cagccccgcc gagctcgggg attggctgag gagggaaaag gcggggcttg   240
aggaaaaaaa tataaacaca gagccgcccc cagggaaaca gcgagcccgg gaagagctgc   300
taagacttcc tctgcggtct gtgagcgcag ccttggcaga tccgttgcct ccgaggacca   360
ccgcgggcag aagcggcgcg ttcggtttcc ggcttcagag ctctcgtctg ggatcccggt   420
ttcgagtcta gaggctgttt gcggagagag caggccagcg ac                      462

<210> SEQ ID NO 3
<211> LENGTH: 462
<212> TYPE: DNA
<213> ORGANISM: Sus scrofa
<220> FEATURE:
<221> NAME/KEY:
<222> LOCATION:
<223> OTHER INFORMATION:
<300> PUBLICATION INFORMATION:
<301> AUTHORS: Chen,M.Y.,
      Huang,S.Y.,
      Tsou,H.L.,
      Lin,E.C.,
      Yang,P.C.,
      Kuo,Y.H.,
      Huang,T.Y.
      Lee,W.C.
<302> TITLE: Polymorphism in the 5'-flanking region of porcine heat
      shock protein 70.2 gene
<303> JOURNAL: Animal Genetics
<304> VOLUME: 31
<305> ISSUE: 6
<306> PAGES: 410-411
<307> DATE: 2000
<308> DATABASE ACCESSION NUMBER: AF139178; GenBank
<309> DATABASE ENTRY DATE: 1999-03-28

<400> SEQUENCE: 3
aacaggtgcc gtgcaaacag cgaacctcca cagcatctct tccccccctcc cttgaggact    60 ccggtttcct cccgcgaatc ccagaagagt ctggagagtt ctgggagggg cggcagccag   120
ggcgctgatt ggccccagaa agccaggggg caggacgcga ggcgaaacct ctggaatatt   180
cccgacctgg cagccccgcc gagctcgggg attggctgag gagggaaaag gagggggcttg   240 aggaaaaaaa tataaacaca gagccgcccc cagggaaaca gcgagcccgg gaagagctgc   300
taagacttcc tctgcggtct gtgagcgcag ccttggcaga tccgctgcct ccgaggacca   360
ccgcgggcag aagcggcgcg ttcggtttcc ggcttcagag ctctcgtctg ggatcccggt   420
ttcgagtcta gaggctgttt gcggagagag caggccagcg ac                      462
```